United States Patent
Sugimoto

(10) Patent No.: US 7,951,981 B2
(45) Date of Patent: May 31, 2011

(54) PROCESS FOR PRODUCING PERFLUOROALKYNE COMPOUND

(75) Inventor: Tatsuya Sugimoto, Tokyo (JP)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 12/225,529

(22) PCT Filed: Mar. 30, 2007

(86) PCT No.: PCT/JP2007/057176
§ 371 (c)(1),
(2), (4) Date: Jul. 21, 2010

(87) PCT Pub. No.: WO2007/114359
PCT Pub. Date: Oct. 11, 2007

(65) Prior Publication Data
US 2010/0292516 A1   Nov. 18, 2010

(30) Foreign Application Priority Data

Mar. 31, 2006   (JP) ................................ 2006-096421

(51) Int. Cl.
*C07C 17/00*   (2006.01)
*C07C 17/02*   (2006.01)
(52) U.S. Cl. .......................... 570/156; 570/154; 570/155
(58) Field of Classification Search .................. 570/154, 570/155, 156
See application file for complete search history.

(56) References Cited

U.S. PATENT DOCUMENTS

| 2005/0092240 A1 | 5/2005 | Sugawara et al. |
| 2005/0101140 A1 | 5/2005 | Yamaguchi et al. |

FOREIGN PATENT DOCUMENTS

| JP | 09-237783 | 9/1997 |
| JP | 2003-146917 | 5/2003 |
| JP | 2004-055680 | 2/2004 |
| JP | 2004-231562 | 8/2004 |
| JP | 2004-292329 | 10/2004 |

OTHER PUBLICATIONS

R. N. Haszeldine, "The Addition of Free Radicals to Unsaturated Systems. Part 1. The Direction of Radical Addition to 3 : 3 : 3—Trifluoropropene," Journal of Chemical Society, 1952, p. 2504-2513.
International Search Report mailed May 15, 2007, issued on PCT/JP2007/057176.

*Primary Examiner* — Jafar Parsa
(74) *Attorney, Agent, or Firm* — Edwards Angell Palmer & Dodge LLP

(57) ABSTRACT

A process for producing a perfluoroalkyne compound includes an addition reaction step of adding $Cl_2$, $Br_2$, or $I_2$ to a compound shown by the formula (1) $CH_3C{\equiv}CR^1$ to obtain a compound shown by the formula (2) $CH_3CX_2CX_2R^1$, a fluorination reaction step of reacting the compound shown by the formula (2) with fluorine gas to obtain a compound shown by the formula (3) $CF_3CX_2CX_2R^2$, and a dehalogenation reaction step of contacting the compound shown by the formula (3) with a metal or an organometallic compound to obtain a perfluoroalkyne compound shown by the formula (4) $CF_3C{\equiv}CR^2$. According to the present invention, a perfluoroalkyne compound can be produced at high productivity and high yield using starting raw materials which are environmentally friendly and industrially available. In the above formulas, $R^1$ represents a methyl group or an ethyl group, X represents Cl, Br, or I, and $R^2$ represents a trifluoromethyl group or a pentafluoroethyl group.

4 Claims, No Drawings

PROCESS FOR PRODUCING PERFLUOROALKYNE COMPOUND

BACKGROUND OF THE INVENTION

1. Field of the Invention

The present invention relates to a highly productive and efficient process for producing a perfluoroalkyne compound useful as a dry-etching gas or a CVD gas used in semiconductor device manufacturing or as a raw material for a fluorine-containing polymer.

2. Description of Related Art

Recently, there has been increased demand for a technology for a dry-etching gas and a CVD gas used in manufacturing semiconductor devices along with an increase in the degree of integration and the performance of semiconductor devices, as seen in very-large-scale integrated (VLSI) circuits, ultra-large-scale integrated (ULSI) circuits, and the like. In order to satisfy such a demand, various compounds having a better quality have been studied.

For example, Patent Document 1 discloses hexafluoro-2-butyne having a triple bond in a molecule as a gas for forming a fluorinated amorphous carbon insulating film having a low dielectric constant. Patent Document 2 discloses that octafluoro-2-pentyne having a triple bond in a molecule is useful as a dry-etching gas for forming a high aspect ratio contact hole.

As a process for preparing a perfluoroalkyne compound having a triple bond in a molecule, Patent Document 3, for example, discloses a process of obtaining a target product, octafluoro-2-pentyne, by treating 2,3-dihydrodecafluoropentane with an alkali.

However, 2,3-dihydrodecafluoropentane used as a raw material has been reported to be harmful to the environment since its atmospheric lifetime is 17 years and its (100-year) global warming potential (GWP) value is as high as 1300.

Non-patent Document 1 discloses the following process of preparing hexafluoro-2-butyne. First, trifluoroiodomethane is added to 3,3,3-trifluoropropene tb obtain 2-iodohexafluorobutane. Then, 2-iodohexafluorobutane is treated with an alkali to obtain hexafluoro-2-butene. Chlorine or bromine is added to hexafluoro-2-butene to obtain 2,3-dihalohexafluorobutane. Finally, 2,3-dihalohexafluorobutane is treated twice with an alkali to obtain hexafluoro-2-butyne.

However, the process disclosed in the document has many problems when manufacturing the product industrially, because trifluoroiodomethane and 3,3,3-trifluoropropene are industrially procured only with difficulty and the process has many production steps. Therefore, the process is not practical.

Patent Document 1: JP-A-9-237783
Patent Document 2: US-A-2005101140
Patent Document 3: US-A-2005092240
Non-patent Document 1: Journal of Chemical Society, p. 2504 (1952)

SUMMARY OF THE INVENTION

The present invention has been achieved in view of the above problems of the related art. An object of the present invention is to provide a highly productive process for producing a perfluoroalkyne compound at a high yield using starting materials which are environmentally friendly and industrially available.

The inventors of the present invention have conducted extensive studies in order to achieve the above object. As a result, the inventors have found that a perfluoroalkyne compound can be obtained at high productivity and high yield by reacting an alkyne compound contained in a C4 or C5 petroleum fraction (starting material) with a specific halogen molecule to halogenate a triple bond, fluorinating, and then contacting with a metal or an organometallic compound to dehalogenate the compound. This finding has led to the completion of the present invention.

According to the present invention, the following process for producing a perfluoroalkyne compound described in [I] to [III] is provided.

[I] A process for producing a perfluoroalkyne compound comprising:

an addition reaction step of adding $Cl_2$, $Br_2$, or $I_2$ to a compound shown by the formula (1) $CH_3C{\equiv}CR^1$ (wherein $R^1$ is a methyl group or an ethyl group) to obtain a compound shown by the formula (2) $CH_3CX_2CX_2R^1$ (wherein $R^1$ is the same as above and X is Cl, Br, or I);

a fluorination reaction step of reacting the compound shown by the formula (2) with fluorine gas to obtain a compound shown by the formula (3) $CF_3CX_2CX_2R^2$ (wherein X is the same as above and $R^2$ is a trifluoromethyl group or a pentafluoroethyl group); and a dehalogenation reaction step of contacting the compound shown by the formula (3) with a metal or an organometallic compound to obtain a perfluoroalkyne compound shown by the formula (4) $CF_3C{\equiv}CR^2$ (wherein $R^2$ is the same as above).

[II] The process according to [I], wherein the dehalogenation reaction step comprises intermittently or continuously feeding the compound shown by the formula (3) to the reaction system while intermittently or continuously discharging the produced perfluoroalkyne compound shown by the formula (4) from the reaction system.

[III] The process according to [I] or [II], wherein the perfluoroalkyne compound shown by the formula (4) is octafluoro-2-pentyne.

According to the present invention, a perfluoroalkyne compound can be produced at high productivity and high yield using starting raw materials which are environmentally friendly and industrially available.

DETAILED DESCRIPTION OF THE INVENTION AND PREFERRED EMBODIMENTS

The process for producing a perfluoroalkyne compound of the present invention comprises the following steps (α) to (γ).

(α) An addition reaction step of adding $Cl_2$, $Br_2$, or $I_2$ to a compound shown by the formula (1) $CH_3C{\equiv}CR^1$ to obtain a compound shown by the formula (2) $CH_3CX_2CX_2R^1$.

(β) A fluorination reaction step of reacting the compound shown by the formula (2) with fluorine gas to obtain a compound shown by the formula (3) $CF_3CX_2CX_2R^2$.

(γ) A dehalogenation reaction step of contacting the compound shown by the formula (3) with a metal or an organometallic compound to obtain a perfluoroalkyne compound shown by the formula (4) $CF_3C{\equiv}CR^2$.

Each step is described below in more detail.

(α) Addition reaction step

In the addition reaction step, the compound shown by the formula (2) is obtained by adding $Cl_2$, $Br_2$, or $I_2$ to the compound shown by the formula (1) (hereinafter referred to from time to time as "alkyne compound").

In the formula (1), $R^1$ represents a methyl group or an ethyl group. In the formula (2), X represents Cl, Br, or I.

In the formula (1), the compound in which $R^1$ is a methyl group is 2-butyne. 2-Butyne is a compound having a triple bond with a boiling point of 26° C. contained in a C4 petroleum fraction.

In the formula (1), the compound in which $R^1$ is an ethyl group is 2-pentyne. 2-Pentyne is a compound having a triple bond with a boiling point of 56° C. contained in a C5 petroleum fraction.

2-Butyne or 2-pentyne may be easily obtained by rectifying the C4 or C5 petroleum fraction by a general method. Commercial products are also available. Furthermore, 2-butyne and 2-pentyne may be prepared by reacting halogenated methyl or halogenated ethyl with methylacetylide which is obtained by contacting a metal such as sodium or lithium with methylacetylene which is produced by purifying the C4 petroleum fraction. 2-Pentyne may also be prepared by reacting halogenated methyl with 1-butynylide which is obtained by contacting a metal such as sodium or lithium with 2-butyne. These compounds have been utilized as raw materials of synthetic fragrances such as leaf alcohol.

$Cl_2$, $Br_2$, or $I_2$ added to the triple bond of the alkyne compound may be used individually or in combination of two or more. It is preferable to use these halogens individually when ease of operation and cost reduction are considered.

$Cl_2$, $Br_2$, or $I_2$ may be used as is or may be diluted with (or dissolved in) an appropriate solvent before use. Specific examples of the solvent include the reaction solvents described later. The solvent may be either the same as or different from the reaction solvent.

The amount of $Cl_2$, $Br_2$, or $I_2$ is preferably 2 to 10 mol, more preferably 2.2 to 5 mol, and particularly preferably 2.5 to 4 mol for 1 mol of the alkyne compound. When any of $Cl_2$, $Br_2$, or $I_2$ are mixed, the term "amount" refers to the amount as a mixture.

The amount of $Cl_2$, $Br_2$, or $I_2$ in the above range is sufficient for the addition reaction to the triple bond of the alkyne compound without leaving unreacted triple bonds, double bonds produced by the addition of only 1 mol of a halogen to the triple bond, or undesired by-products produced by substitution of a hydrogen atom in some C-H bonds with Cl, Br, or I, which is a reaction other than the addition reaction to the triple bond.

Additives such as Lewis acid may be added to the reaction system in order to promote the addition reaction. Examples of the additives include aluminum chloride, ferric chloride, antimony chloride, zinc chloride, stannic chloride, aluminum bromide, iron bromide, antimony bromide, and zinc bromide. The amount of the additives is usually 0.001 to 0.3 equivalents, and preferably 0.01 to 0.2 equivalents for one equivalent of the alkyne compound as a starting material.

The temperature of the addition reaction is usually −100 to +100° C., and preferably −80 to +70° C. If the temperature is within the above range, the reaction rate is sufficient in practice and undesired byproducts are not produced.

The addition reaction may be carried out using or without using a solvent. It is preferable to carry out the reaction using a solvent when improvement of the reaction yield is considered.

The solvent is not particularly limited insofar as it does not adversely affect the addition reaction. A halogen-containing solvent such as methylene chloride, chloroform, carbon tetrachloride, and 1,1,2-trichlorotrifluoroethane is preferable when improvement of the reaction yield is considered. Carbon tetrachloride is particularly preferable.

The amount of the solvent is preferably 10 to 2000 parts by weight, more preferably 100 to 1000 parts by weight, and particularly preferably 300 to 600 parts by weight for 100 parts by weight of the alkyne compound when improvement of the reaction rate and the reaction yield is considered.

There are no specific limitations to the method of the addition reaction. When using $Cl_2$, for example, a reaction vessel equipped with a stirrer is charged with the alkyne compound and the solvent, and $Cl_2$ gas is blown into the vessel while stirring.

When using $Br_2$ or $I_2$, a reaction vessel equipped with a stirrer is charged with the alkyne compound and the solvent, and $Br_2$ or $I_2$ is added dropwise to the vessel while stirring.

$Cl_2$, $Br_2$, or $I_2$ may be used as is or may be diluted with (or dissolved in) a solvent before use. The same solvent mentioned above may be used as the solvent. The solvent may be either the same as or different from the solvent added to the vessel together with the alkyne compound.

The reaction is completed when the target material (the compound shown by the formula (2)) is produced and the alkyne compound (raw material, 2-butyne or 2-pentyne) has been consumed, which may be confirmed by analyzing the reaction mixture using a known analyzing method such as gas chromatography.

After the completion of the addition reaction, unreacted $Cl_2$, $Br_2$, or $I_2$ is removed by adding a reducing agent such as sodium thiosulfate and sodium hydrogensulfite, as is or as an aqueous solution, to the reaction mixture. The target material may be isolated by purification such as extraction with an organic solvent, alkaline cleaning, washing with water, drying, and distillation according to the usual treatment method.

The compound shown by the formula (2) is sent to the next fluorination reaction step after purification or isolation or without purification.

(β) Fluorination Reaction Step

In the fluorination reaction step, the compound shown by the formula (3) is obtained by reacting the compound shown by the formula (2) obtained in the addition reaction step with fluorine gas ($F_2$).

In the formula (3), $R^2$ represents a trifluoromethyl group or a pentafluoroethyl group.

The compound shown by the formula (3), wherein $R^2$ is a trifluoromethyl group, may be obtained from the compound shown by the formula (2), wherein $R^1$ is a methyl group; and the compound shown by the formula (3), wherein $R^2$ is a perfluoroethyl group, may be obtained from the compound shown by the formula (2), wherein $R^1$ is an ethyl group.

The amount of the fluorine gas may be the amount required for conversion of six C—H bonds (when 2-butyne is used as a raw material) or eight C—H bonds (when 2-pentyne is used as a raw material) of the compound shown by the formula (2) to C—F bonds.

Specifically, the amount of fluorine gas is usually 8 mol or more, preferably 20 mol or more, and more preferably 100 mol or more for 1 mol of the compound shown by the formula (2).

The reaction is presumed to be a radical reaction. When the amount of fluorine gas is within the above range, the reaction may proceed while sufficiently suppressing isomerization reaction.

The temperature of the fluorination reaction is usually −100 to +50° C., preferably −80 to +30° C., and more preferably −70 to −20° C. If the temperature is within the above range, the reaction rate is sufficient in practice and undesired byproducts are not produced.

The fluorination reaction is preferably carried out in a solvent. The solvent is not particularly limited insofar as the solvent does not adversely affect the fluorination reaction. Examples of the solvent include perfluorocarbons such as perfluoroheptane, perfluorooctane, perfluorononane, and perfluoro(2-n-butyl-tetrahydrofuran) and chlorofluorocarbons such as 1,1,2-trichlorotrifluoroethane and 1,1,1-trichlorotrifluoroethane. Perfluorooctane and 1,1,2-trichlorotrifluoroethane are preferable and 1,1,2-trichlorotrifluoroethane is particularly preferable because the target material (compound shown by the formula (3)) may be produced at high reaction rate and high yield.

Although not particularly limited, the solvent is usually used in an amount of 200 to 1000 parts by weight, and preferably 300 to 500 parts by weight for 100 parts by weight of the compound shown by the formula (2).

One example of the method of fluorination reaction comprises charging a reaction vessel equipped with a stirrer with the compound shown by the formula (2) and the solvent, and bubbling fluorine gas into the reaction mixture through an inner tube installed in the vessel while stirring.

It is preferable to use a reaction vessel which is not corroded by the fluorine gas or hydrogen fluoride which is produced by the reaction. For example, a reaction vessel made of a material such as stainless steel, hastelloy, or nickel is preferably used.

The fluorine gas is preferably sent to the reaction vessel after dilution with an inert gas such as nitrogen or helium. The amount of the inert gas may be appropriately selected according to the reaction conditions, from a range preferably of 2 to 100 mol, more preferably of 3 to 30 mol, and particularly preferably of 5 to 15 mol per 1 mol of the fluorine gas.

When the fluorine gas is diluted or a gas diluted at the above rate is used, the fluorination reaction does not proceed too rapidly, and decomposition of the raw material and generation of unnecessary byproduct do not occur. Also, the target material may be obtained at high reaction rate and high yield if the diluted gas is used in the above-mentioned amount.

When the fluorination reaction is completed, the unreacted fluorine gas is discharged from the reaction vessel. Therefore, the completion of the reaction may be confirmed by a rapid increase in the concentration of the fluorine gas in the gas discharged from the reaction vessel. The gas may be discharged to the atmosphere through a scrubber filled with an alkaline solution.

Since the fluorination reaction is highly exothermic, the reaction is carried out at a low temperature as mentioned above. However, there still is a possibility that the raw materials and the partially-fluorinated compounds will evaporate and be mixed into the vapor phase in the reaction vessel when heat is generated. This causes an undesirable vigorous reaction with fluorine gas in the vapor phase such as decomposition and tarring which may result in a yield decrease. Therefore, it is desired to install a condenser on the reaction vessel to avoid such a phenomenon. The condenser cools and liquefies the evaporated materials or the partially-fluorinated compounds before recycling to the reaction vessel.

It is preferable to remove the hydrogen fluoride contained in the gas from the reaction vessel before discharging to the atmosphere. As an example of the removing method, a method of passing the gas through a column which is filled with a hydrogen fluoride scavenger at the outlet of the reaction vessel to trap the hydrogen fluoride produced by the fluorination reaction can be given. When considering safety, it is preferable to install a scrubber filled with an alkaline solution after the column filled with the hydrogen fluoride scavenger.

As examples of the hydrogen fluoride scavenger to fill in the column, alkali metal fluorides such as sodium fluoride and potassium fluoride and silica gel can be given. Sodium fluoride is particularly preferable.

The fluorine gas remaining in the reaction vessel after the reaction is purged by an inert gas such as nitrogen or helium. It is preferable to add the hydrogen fluoride scavenger such as sodium fluoride and silica gel to the reaction mixture because there is a possibility that the hydrogen fluoride will still remain in the reaction mixture. Then, the target compound shown by the formula (3) may be isolated by purification such as distillation after the usual post treatment of alkaline cleaning, washing with water, drying, and the like.

The compound shown by the formula (3) may be sent to the next dehalogenation reaction step either after purification or isolation or without purification.

(γ) Dehalogenation Reaction Step

In the dehalogenation reaction step, the compound shown by the formula (3) is contacted with a metal or an organometallic compound to carry out the dehalogenation reaction and obtain a perfluoroalkyne compound shown by the formula (4).

The term "dehalogenation reaction" refers to the reaction of removing Cl, Br, or I from the compound shown by the formula (3).

Although there are no specific limitations to the metal or the organometallic compound to be used insofar as it has a capability of dehalogenation, the metal is preferred.

As the metal used, at least one metal selected from the group consisting of Zn, Mg, Cu, Al, Li, and Na is preferable when improvement of the reaction yield and the reaction rate is considered. Zn is more preferable. When Zn, Mg, Cu, or Al is used as the metal, it is preferable to use these metals in a cut or powdered form when improvement of the reaction yield and the reaction rate is considered. It is more preferable to previously activate the surface of the metal with an activator such as an organic acid (e.g. acetic acid, propionic acid), $I_2$, or 1,2-dibromoethane before carrying out the reaction. The reaction may be carried out by adding the metal and the activator to the reaction system without previously activating the surface of the metal.

As the organometallic compound, an alkyl lithium, an alkyl magnesium halide, and an aryl magnesium halide are preferable when improvement of the reaction yield and the reaction rate is considered.

Specific examples of the alkyl lithium include methyl lithium, n-butyl lithium, sec-butyl lithium, t-butyl lithium, phenyl lithium, lithiumhexamethyl disilazid, and the like.

Specific examples of the alkyl magnesium halide include methyl magnesium bromide, ethyl magnesium bromide, ethyl magnesium iodide, and the like.

Specific examples of the aryl magnesium halide include phenyl magnesium bromide and the like.

Those metals and the organometallic compounds may be used individually or in combination of two or more, but using one metal or one organometallic compound alone is preferable.

Although it is not particularly limited, the amount of the metals or the organometallic compounds is preferably 2 to 10 equivalents, and more preferably 3 to 5 equivalents for one equivalent of the compound shown by the formula (3) when improvement of the reaction yield and the reaction rate is considered.

The temperature of dehalogenation reaction is usually 25 to 250° C., and preferably 50 to 150° C. If the temperature is within this range, the reaction rate is sufficient in practice and undesired byproducts are not produced.

The dehalogenation reaction is preferably carried out in a solvent.

When the metal is used for the reaction, the solvent preferably used to improve the reaction yield and the reaction rate includes alcohols such as methanol, ethanol, n-propanol, isopropanol, sec-butanol, t-butanol, t-amyl alcohol, propylene glycol monomethyl ether, and diethylene glycol monomethyl ether; ethers such as tetrahydrofuran, 1,4-dioxane, dibutyl ether, diethylene glycol dimethyl ether, 1,2-dimethoxy ethane, cyclopentyl methyl ether, and triethylene glycol dimethyl ether; nitrogen-containing organic compounds such as N,N-dimethylformamide, N,N-dimethylacetamide, N-methylformanilide, and N-methyl pyrrolidone; and sulfur-containing organic compounds such as dimethyl sulfoxide, sulfolane, and propane sultone. Ethers are more preferable.

When the organometallic compound is used for the reaction, the solvent preferably used to improve the reaction yield and the reaction rate is an ether such as diethyl ether, tetrahydrofuran, 1,4-dioxane, dibutyl ether, 1,2-dimethoxy ethane, and cyclopentyl methyl ether.

These solvents may be used either individually or in combination of two or more.

Although not particularly limited, the solvent is usually used in an amount of 100 to 1000 parts by weight, and preferably 200 to 600 parts by weight for 100 parts by weight of the compound shown by the formula (3).

There are no particular limitations to the method of halogenation reaction. One example comprises adding a metal or an organometallic compound and a solvent to a reaction vessel equipped with a stirrer and adding dropwise the compound shown by the above formula (3) (or a solution of the compound shown by the above formula (3), for example, the reaction product obtained in the step (2)) to the mixture while stirring.

A perfluoroalkyne compound shown by the formula (4), that is, hexafluoro-2-butyne (when 2-butyne is used as a raw material) or octafluoro-2-pentyne (when 2-pentyne is used as a raw material) is obtained by the dehalogenation reaction. The boiling point of hexafluoro-2-butyne is −24° C., and the boiling point of octafluoro-2-pentyne is 5° C. These compounds are gaseous under normal pressure and have a boiling point lower than the boiling point of the compound shown by the formula (3). Accordingly, in order to improve productivity, it is desirable that the perfluoroalkyne compound be removed from the reaction system intermittently or continuously as produced and be collected in a cooled trap.

A method of intermittently or continuously feeding the compound shown by the formula (3) to the reaction system while intermittently or continuously removing the produced perfluoroalkyne compound from the reaction system can be given as an example of the method for the reaction. The (intermittent or continuous) method used for feeding the compound shown by the formula (3) and the (intermittent or continuous) method used for removing the perfluoroalkyne compound may be the same or different.

Specifically, by using a reaction system consisting of a reaction vessel equipped with a stirrer and a distillation column, the compound shown by the formula (3) (or a solution of the compound shown by the formula (3)) is intermittently or continuously fed to a mixture of a metal or an organometallic compound and a solvent in the reaction vessel while stirring to carry out the dehalogenation reaction, and, at the same time, the produced perfluoroalkyne compound is intermittently or continuously removed from the top of the column to collect the compound in a cooled trap. The reaction system, that is, the reaction site to carry out the dehalogenation reaction is the reaction vessel.

The rate of feeding the compound shown by the formula (3) (or the solution of the compound shown by the formula (3)) may be set according to the rate of removing (distillation of) the produced perfluoroalkyne compound. Decrease of the yield may be suppressed by controlling overfeeding. Although the rate of feeding the compound shown by the formula (3) (or the solution of the compound shown by the formula (3)) to the reaction system varies according to the type of the reaction system or the scale of the reaction, such a rate (mol/hr) is preferably three times or less the rate (mol/hr) of removing the produced perfluoroalkyne compound. It is desired to adjust the rate of removing by controlling the temperature at the top of the distillation column.

The dehalogenation reaction is for obtaining a perfluoroalkyne compound by forming a triple bond by causing four halogen atoms to be separated from the compound shown by the formula (3).

When the perfluoroalkyne compound is intermittently or continuously removed from the reaction system while the dehalogenation reaction is carried out, a compound having two remaining halogen atoms produced during the reaction (intermediate compound) may accompany the perfluoroalkyne compound. Because the intermediate compound has a boiling point higher than the boiling point of the target material (perfluoroalkyne compound), it is possible to return the intermediate compound to the reaction system via the distillation column. Accordingly, the decrease of productivity caused by the intermediate compound accompanying the target compound may be prevented.

The theoretical number of distillation columns is preferably five or more when efficiency of sending the intermediate compounds back to the reaction system is considered.

The perfluoroalkyne compound collected in the trap may be purified by distillation or the like according to a known method to obtain a product with high purity.

The intended perfluoroalkyne compound may be obtained by the above process. The process of the present invention is particularly suitable for producing octafluoro-2-pentyne.

EXAMPLES

The present invention will be described in more detail by way of examples, which should not be construed as limiting the present invention. In the following examples, "parts" and "%" respectively refer to "parts by weight" and "wt%" unless otherwise indicated.

Analysis conditions were as follows.
(1) Gas Chromatography Analysis (GC Analysis)
Equipment: "HP-6890" manufactured by Hewlett-Packard Company, L.P.
Column: "Neutrabond-1" 60 m×I. D 0.25 μm, 1.5 μm df, manufactured by GL Science Inc.
Column temperature: 40° C. (10 minutes), heated at 20° C./min, then 240° C. (10 minutes)
Injection temperature: 200° C.
Carrier gas: nitrogen gas
Detector: FID
(2) Gas Chromatography/Mass Spectrometry Analysis (GC-MS Analysis)
GC part: "HP-6890" manufactured by Hewlett-Packard Company, L.P.
Column: "Neutrabond-1" 60 m×I. D 0.25 μm, 1.5 μm df, manufactured by GL Science Inc.
Column temperature: 40° C. (10 minutes), heated at 20° C./min, then 240° C. (10 minutes)
Injection temperature: 200° C.
Carrier gas: nitrogen gas
Detector: FID
MS part: "5973 NETWORK" manufactured by Hewlett-Packard Company, L.P.
Detector: EI type (accelerating voltage: 70 eV)

(3) NMR Analysis
Equipment: $^{19}$F/$^{13}$C-NMR analyzer "JNM-ECA-500" manufactured by JEOL Ltd.

Example 1

Production of octafluoro-2-pentyne (1) Addition reaction of chlorine to 2-pentyne (addition reaction step)

A round-bottom glass flask (reaction vessel) equipped with a stirrer and a chlorine gas feed pipe was charged with 68 parts of 2-pentyne (purity: 96%, manufactured by Tokyo Chemical Industry Co., Ltd.), 0.7 parts of iron (III) chloride, and 300 parts of carbon tetrachloride. The reaction vessel was immersed in a dry ice-ethanol bath to cool to −30° C. While stirring the solution in the reaction vessel, 426 parts of chlorine gas were bubbled into the carbon tetrachloride solution from a chlorine cylinder at approximately 3 ml/min.

After confirming by gas chromatography analysis that the raw material (2-pentyne) was consumed, the temperature of the reaction solution was allowed to increase to room temperature. To remove the unreacted chlorine gas, nitrogen gas was blown into the system at a rate of 10 ml/min for approximately 15 minutes, 200 parts of a 5% sodium hydrogensulfite solution was added to the reaction solution, and the solution was stirred for about five minutes. Then, the reaction mixture was transferred to a separating funnel to separate the lower layer (layer of the carbon tetrachloride solution). The layer of the carbon tetrachloride solution was washed with a saturated sodium bicarbonate aqueous solution, then with a saturated brine, and dried overnight on anhydrous magnesium sulfate. Magnesium sulfate was separated by filtration to obtain a filtrate. Carbon tetrachloride was removed from the filtrate by using a rotary evaporator to obtain a crude 2,2,3,3-tetrachloropentane. The crude 2,2,3,3-tetrachloropentane was distilled under reduced pressure to obtain 178 parts of 2,2,3,3-tetrachloropentane having a purity of 98% (yield: 85%).

(2) Fluorination reaction of 2,2,3,3-tetrachloropentane (fluorination reaction step)

A Hastelloy autoclave (reaction vessel) equipped with a stirrer and a condenser was charged with 130 parts of 1,1,2-trichlorotrifluoroethane and 30 parts of 2,2,3,3-tetrachloropentane obtained in the addition reaction step, and the reaction vessel was immersed in a dry ice-ethanol bath to cool to −70° C. A refrigerant at −20° C. was circulated through the condenser. A dry nitrogen gas was caused to flow in the reaction vessel at 10 ml/min for 30 minutes. Then, a mixture of dry nitrogen gas (flow rate: 30 ml/min) and fluorine gas (manufactured by Kanto Denka Kogyo Co., Ltd., flow rate: 3 ml/min) was bubbled into the reaction vessel through a mass flow control valve to react for 10 hours.

After the reaction, feeding of the fluorine gas was stopped, and the excessive fluorine gas was discharged by causing dry nitrogen gas to flow at 10 ml/min for 15 minutes. 30 parts of pulverized sodium fluoride was added to the reaction vessel and stirred for 10 minutes. Sodium hydrogen difluoride was separated by filtration to obtain a filtrate. 1,1,2-Trichlorotrifluoroethane was removed from the filtrate by using a rotary evaporator to obtain a crude 2,2,3,3-tetrachlorooctafluoropentane. Fractions having a boiling point of 149 to 151° C. were collected from the crude 2,2,3,3-tetrachlorooctafluoropentane under normal pressure to obtain the target material, 2,2,3,3-tetrachlorooctafluoropentane, in an amount of 26 parts (purity: 97%) at a yield of 52%.

(3) Dechlorination Reaction of 2,2,3,3-tetrachlorooctafluoropentane (Dehalogenation Reaction Step)

A stainless steel autoclave (reaction vessel) equipped with a stirrer, a dropping funnel, and a distillation column (theoretical number of columns: approx. 7) was charged with 90 parts of diethylene glycol dimethyl ether, 10 parts of zinc powder, and 1 part of iodine. The reaction vessel was heated to 50° C. and the mixture was stirred for 20 minutes. 41 parts of a solution containing 31 parts of the 2,2,3,3-tetrachlorooctafluoropentane obtained at the fluorination reaction step dissolved in 20 parts of diethylene glycol dimethyl ether was added dropwise using a dropping funnel while the reaction temperature was gradually increased to 80° C. When the temperature at the top of the distillation column had reached about 5° C., the product was removed from the top of the distillation column at a reflux ratio of 5:1 and collected in a glass trap cooled to −70° C. After the dropwise addition was completed, the stirring was continued for a further 30 minutes and the reaction temperature was increased to 120° C. to discharge the product from the reaction vessel and collect it in the glass trap. The product collected in the glass trap was analyzed by gas chromatography. As a result, it was confirmed that 13 parts of the target product, octafluoro-2-pentyne, was obtained at a yield of 71%. The octafluoro-2-pentyne obtained was analyzed by NMR and GC-MS analysis. The results are shown below.

$^{19}$F-NMR (CDCl$_3$, standard peak CFCl$_3$): −54.1 (3F), −86.0 (3F), −106.4 (2F)

$^{13}$C-NMR (CDCl$_3$, standard peak TMS): 72.18, 77.31, 105.4, 113.9, 118.4

GC-MS (m/z): 212, 193, 143, 124, 93, 69

The target product, octafluoro-2-pentyne, was produced at a high yield using 2-pentyne as a raw material. These Examples show usability of an alkyne compound having a triple bond contained in a C5 petroleum fraction as a raw material in the production of a perfluoroalkyne compound.

What is claimed is:

1. A process for producing a perfluoroalkyne compound comprising:
    an addition reaction step of adding Cl$_2$, Br$_2$, or I$_2$ to a compound shown by the formula (1) CH$_3$C≡CR$^1$ (wherein R$^1$ is a methyl group or an ethyl group) to obtain a compound shown by the formula (2) CH$_3$CX$_2$CX$_2$R$^1$ (wherein R$^1$ is the same as above and X is Cl, Br, or I);
    a fluorination reaction step of reacting the compound shown by the formula (2) with fluorine gas to obtain a compound shown by the formula (3) CF$_3$CX$_2$CX$_2$R$^2$ (wherein X is the same as above and R$^2$ is a trifluoromethyl group or a pentafluoroethyl group); and
    a dehalogenation reaction step of contacting the compound shown by the formula (3) with a metal or an organometallic compound to obtain a perfluoroalkyne compound shown by the formula (4) CF$_3$C≡CR$^2$ (wherein R$^2$ is the same as above).

2. The process according to claim 1, wherein the dehalogenation reaction step comprises intermittently or continuously feeding the compound shown by the formula (3) to the reaction system while intermittently or continuously discharging the produced perfluoroalkyne compound shown by the formula (4) from the reaction system.

3. The process according to claim 1, wherein the perfluoroalkyne compound shown by the formula (4) is octafluoro-2-pentyne.

4. The process according to claim 2, wherein the perfluoroalkyne compound shown by the formula (4) is octafluoro-2-pentyne.

* * * * *